United States Patent

Kobuch et al.

(10) Patent No.: US 6,372,243 B2
(45) Date of Patent: *Apr. 16, 2002

(54) LOW-OXYGEN FLUOROCARBON AS AN AGENT FOR OPHTHALMOLOGY

(75) Inventors: Karin Kobuch, Pentling; Veit-Peter Gabel, Regensburg; Joachim Dresp, Munich; Dirk-Henning Menz, Diedorf, all of (DE)

(73) Assignee: Pharm pur GmbH, Augsburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/270,562

(22) Filed: Mar. 16, 1999

(30) Foreign Application Priority Data

Mar. 18, 1998 (DE) .......................... 198 11 683

(51) Int. Cl.⁷ .................................................. A61F 2/02
(52) U.S. Cl. ....................................................... 424/423
(58) Field of Search ......................................... 424/423

(56) References Cited

U.S. PATENT DOCUMENTS

| | | |
|---|---|---|
| 3,911,138 A | 10/1975 | Clark, Jr. |
| 4,378,797 A | 4/1983 | Osterholm |
| 4,393,863 A | 7/1983 | Osterholm |
| 4,445,500 A | 5/1984 | Osterholm |
| 4,445,514 A | 5/1984 | Osterholm |
| 4,445,886 A | 5/1984 | Osterholm |
| 4,445,887 A | 5/1984 | Osterholm |
| 4,445,888 A | 5/1984 | Osterholm |
| 4,446,154 A | 5/1984 | Osterholm |
| 4,446,155 A | 5/1984 | Osterholm |
| 4,450,841 A | 5/1984 | Osterholm |
| 4,451,251 A | 5/1984 | Osterholm |
| 4,490,351 A | 12/1984 | Clark, Jr. |
| 4,514,500 A | 4/1985 | Giaever et al. |
| 4,657,532 A | 4/1987 | Osterholm |
| 4,686,085 A | 8/1987 | Osterholm |
| 4,758,431 A | 7/1988 | Osterholm |
| 4,795,423 A | 1/1989 | Osterholm |
| 4,865,836 A | 9/1989 | Long, Jr. |
| 4,866,096 A | 9/1989 | Schweighardt |
| 4,963,130 A | 10/1990 | Osterholm |
| 4,981,691 A | 1/1991 | Osterholm et al. |
| 5,037,384 A | 8/1991 | Chang |
| 5,085,630 A | 2/1992 | Osterholm et al. |
| 5,149,321 A | 9/1992 | Klatz et al. |
| 5,158,536 A | 10/1992 | Sekins et al. |
| 5,213,570 A | 5/1993 | VanDeripe |
| 5,275,669 A | 1/1994 | Van Der Puy et al. |
| 5,374,624 A | 12/1994 | Segel |
| 5,393,513 A | 2/1995 | Long, Jr. |
| 5,397,805 A | 3/1995 | Meinert |
| 5,441,733 A | 8/1995 | Meinert |
| 5,563,306 A | 10/1996 | Meinert |
| 5,584,804 A | 12/1996 | Klatz et al. |
| 5,637,318 A | 6/1997 | Gross et al. |
| 5,643,601 A | 7/1997 | Gross et al. |
| 5,824,703 A | 10/1998 | Clark, Jr. |
| 5,827,222 A | 10/1998 | Klatz et al. |
| 5,851,544 A | 12/1998 | Penska et al. |
| 5,859,068 A | 1/1999 | Wilson |
| 5,885,564 A | 3/1999 | Zastrow et al. |

FOREIGN PATENT DOCUMENTS

CA 2232880 8/1996

OTHER PUBLICATIONS

Local Effects of Different Perfluorochemical Agents, Graef's Arch Clin Exp Ophthalmol (1995), Laboratory Investigation, A.J. Augustin et al, pp. 45–47.

Afluorous Biphasic Systems (FBS)—die neue Phasentrennund Immobilisiertechnik—Boy Cornils, Angew. Chem. 1997, 109, Nr. 19, pp. 2147–2149.

Properties and Biomedical Applications of Perfluorochemicals and Their Emulsions, Kenneth C. Lowe, Organofluorine Chemistry:Principles and Commerical Applications, Plenum Press, N.Y., 1994.

Wilson et al., "Perfluorinated Organic Liquid as an Intraocular Oxygen reservoir for the Ischemic Retina", Investigative Ophthamology & Visual Science, Jan. 1995, vol. 36, No. 1, pp. 131–141.

*Primary Examiner*—Carlos A. Azpuru
(74) *Attorney, Agent, or Firm*—Larson & Taylor PLC

(57) ABSTRACT

The present invention concerns fluorocarbons for use in ophthalmology. Fluorocarbons disclosed in the prior art can only be left in the eye for a limited period of time because they cause damage to the retina or intraocular structure. The present invention provides an oxygen-fluorocarbon mixture having a dissolved oxygen content of less than 6% by volume, which can be used as an ophthalmological agent for longer periods of time than conventional fluorocarbons, with little or no damage to the retina or intraocular structures. The invention also provides a process for preparing the oxygen-fluorocarbon mixture. In one embodiment, up to 20% by volume of a second gas, such as carbon dioxide or nitric oxide, is combined with the oxygen-fluorocarbon mixtures.

26 Claims, No Drawings

LOW-OXYGEN FLUOROCARBON AS AN AGENT FOR OPHTHALMOLOGY

FIELD OF INVENTION

The invention concerns the use of a fluorocarbon as an agent for ophthalmology.

BACKGROUND OF THE INVENTION

Within the meaning of this description, the term "fluorocarbon" either refers to compounds from the class of saturated, perfluorinated hydrocarbons in which all of the hydrogen atoms are replaced by fluorinated atoms, or partially fluorinated alkanes having the general formula $R_F R_H$ or $R_F R_H R_F$ that can be present in a liquid or gel-like state. In this case, $R_F$ is a perfluorinated alkyl group and $R_H$ an alkyl group. Substances of this type, as well as their possible applications in medicine and technology are, for example, described in DE 42 05 341 A1, U.S. Pat. No. 5,275,669, U.S. Pat. No. 4,490,351, EP 493 677 A2 and DE 195 36 504 A1.

These fluorocarbons are almost always saturated with oxygen in a highly concentrated manner, whereby the oxygen is present in a physical solution. When increasing the partial pressure of the oxygen, fluorocarbons can store up to 50% by volume of oxygen. This compound-typical property was the basis for the development of numerous technical applications of these compounds (see the article by B. Cornils "Fluorous biphasic systems" in Angew. Chemie [Applied chemistry]1997, 109, 2147), as well as medical applications, e.g. as blood substitutes, as means for liquid artificial respiration, as oxygen carriers in ointments, etc. Fluorocarbons having a low content of dissolved oxygen spontaneously and very quickly absorb oxygen in contact with air until a balance between dissolved oxygen and the oxygen content of the ambient atmosphere is reached. These medical applications of fluorocarbons as oxygen carriers were described, for example, in the aforementioned publications and in the paper by K. C. Lowe "Properties and Biomedical Applications of PFC and their Emulsions", in Org. Fluorine Chem.: Principles and Commercial Appl., Plenum Press, N.Y. 1994.

Moreover, the application of fluorocarbons as an agent in ophthalmology has been described, for example, in the European Patent Application 563 446 A1. In particular, fluorocarbons are used as retina tampons when treating retinal detachments, where their density and their surface properties are of special significance.

So that it can be used as an ophthalmological agent via an intraoperative treatment, the fluorocarbons have to be left in the eye socket for a longer time instead of the vitreous body previously removed, e.g. in order to exert a constant, permanent pressure on the retina.

However, it has been shown that the known fluorocarbons can only be left in the eye for a limited period of time, see U.S. Pat. No. 5,037,384. That is, damage to the retina and the vessel system occur after only a short duration in the eye, the cause of which is to a great extent unknown and is, inter alia, attributed to the high density of the compounds. Due to the strong binding energy between carbon and fluorine, the fluorocarbons are chemically inert and are therefore not broken down by metabolical reactions.

To date, no importance has been ascribed to the quantity of oxygen usually dissolved in the fluorocarbons when the retina and adjacent intraocular structures are damaged. To the extent that this subject has been discussed at all in the literature, e.g. in the paper by A. J. Augustin, M. Spitznas, F. H. J. Koch, T. Böker, J. Lutz in Graefes Arch. Clin. Exp. Ophthalm. 1995, 233, 45–27, "Local Effects of Different Perfluorochemical Agents", the conclusion was that the damage to the retina and the intraocular system observed in animal experiments had to be caused by other factors, e.g. by the tensides contained in the emulsions. This was reinforced in the paper which indicated that toxic effects could not be observed when using pure fluorocarbons (that nevertheless contained oxygen).

In other studies also, damage caused by fluorocarbons was ascribed to other properties of these substances and not to their dissolving power for oxygen. On the contrary, the oxygen solvency of these substances was repeatedly described as an advantage for ophthalmological applications.

SUMMARY OF THE INVENTION

Accordingly, this invention seeks to provide an agent for ophthalmology which can be used for a longer period of time than conventional fluorocarbons, with little or no damage to the retina and adjacent intraocular structures.

Thus, this invention provides an oxygen-physiologically acceptable fluorocarbon composition wherein the content of dissolved oxygen is less than 6%; and the fluorocarbon is chosen from compounds from the class of saturated, perfluorinated hydrocarbons in which all of the hydrogen atoms are replaced by fluorinated atoms, or partially fluorinated alkanes having the general formula $R_F R_H$ or $R_F R_H R_F$ that can be present in a liquid or gel-like state. In this case, $R_F$ is a perfluorinated alkyl group and $R_H$ an alkyl group. In one embodiment, the mixture also contains 0 to 20% by volume of a second gas, such as carbon dioxide or nitric oxide.

This invention also provides a process of creating an oxygen-physiologically acceptable fluorocarbon composition, wherein the content of dissolved oxygen is less than 6%.

In another aspect, this invention provides the use of a physiologically acceptable fluorocarbon having a dissolved oxygen content of less than 6% by volume as an agent for ophthalmology. In particular, said fluorocarbon may be used as an intraocular agent, a retina tampon, an agent for treating ischemic retinal disorders, or as a vitreous body replacement.

An advantage of fluorocarbons having a dissolved oxygen content of less than 6% by volume is that it appears that they can be used as an ophthalmological agent for longer periods of time than conventional fluorocarbons, with little or no damage to the retina or intraocular structures.

DETAILED DESCRIPTION OF THE INVENTION

The inventors recognized that the toxic effect during long-term applications can be ascribed to a considerable content of the physically dissolved oxygen (with a simultaneously low content of dissolved carbon dioxide) in the fluorocarbons. This is in contradiction to the teachings of the prior art.

Our studies have shown that fluorocarbons whose oxygen contents were not carefully reduced resulted in damage to the retinal blood vessels after having been inserted into the vitreous area of the eye of a rabbit. In fluorescence angiography, a narrowing of the vessels appears from the second post-operative day. As time passes, vessel occlusions, a rarefaction of the capillary bed and the development of microaneurisms appear. Histologically, flat preparations of the retinal blood vessels exhibit caliber fluctuations in the area of the vascular walls and a loss of pericytes and endothelial cells from the vascular walls. On the other hand, control tests with deoxygenated fluorocarbons according to the present invention showed normal retinal blood vessels.

Under normal conditions and in a pure oxygen atmosphere, fluorocarbons exhibit a high constituent of physically dissolved oxygen. This is up to 50% by volume. In ordinary ambient air, the oxygen content is still at about 8% by volume. To produce fluorocarbons with a relatively low oxygen content required according to the present invention, the fluorocarbons must first be deoxygenated. It should then be ensured that the low oxygen content obtained during deoxygenation is maintained until the fluorocarbons are used.

Known rinsing processes with gases other than oxygen can be used as suitable processes for the deoxygenation, whereby rinsing can be improved by gentle heating and/or successive evacuating and gas rinsing.

Especially effective are processes for deoxygenation using oxygen getters in a heterogeneous phase. Low-valence metal oxides, in particular reduced $Cu_2O$, which have previously been primarily used for oxygen separation from gases, are especially suitable as heterogeneous oxygen getters. The heterogeneous oxygen getters can thereby be used as a filling for absorber cartridges through which the fluorocarbons are led. If these absorber cartridges are combined with sterile filters, then the fluorocarbon can be deoxygenated immediately prior to being used as an ophthalmological agent.

Due to the very strong solvency of the fluorocarbons for oxygen, it should be ensured that, once the fluorocarbons have been deoxygenated, they remain in an oxygen-lacking state until their use, which is usually only possible by hermetic sealing.

To ensure that fluorocarbons that are otherwise packaged, e.g. in bottles, also remain low-in-oxygen until their use, the aforementioned heterogeneous oxygen getters can also be added to the fluorocarbons. In this case, however, the oxygen getters should be separated immediately prior to use of the fluorocarbons as an agent in ophthalmology which can, for example, be accomplished by filtration.

Alternatively thereto, the heterogeneous oxygen getters can be placed in the projecting gas chamber, whereby its action of maintaining the deoxygenated condition can unfold by means of diffusion processes via a gas phase. A further advantage of using heterogeneous oxygen getters is that partial pressure of other dissolved gases can be set extremely well, which cannot be accomplished in deoxygenation by means of flowing gases without special additional processes. Thus, the content of other physically dissolved gases such as nitrogen, carbon dioxide, or nitric oxide can be easily set to the value that is most advantageous for the respective application.

If, after complete deoxygenation of the fluorocarbons, one wishes a specific, defined oxygen concentration, then this can be obtained by proportionately mixing with the same substance that has, however, been stored in air and thus enriched with oxygen, since the equilibrium concentration of the oxygen in the fluorocarbon stored under atmospheric conditions is a very stable and reproducible value, and is 8% by volume.

A value that differs from zero of the oxygen content of the fluorocarbons is recommended e.g. in an ischemic retina to which oxygen should deliberately be supplied, however, not so much that a toxic injury to the retina occurs.

Furthermore, the oxygen-lacking fluorocarbon can also be mixed with other gases, for example, with nitrogen, carbon dioxide, or nitric oxide (NO). Enrichment with carbon dioxide/nitric oxide is medically of particular significance because an autoregulation system acts in cerebral blood vessels, including the retinal vessels, which reacts to an increased carbon dioxide or nitric oxide content with a vessel dilatation and an increased blood flow. For example, a partial pressure of carbon dioxide corresponding to the air concentration sets in in fluorocarbons. However, in contrast to oxygen, this is below physiological values. While carbon dioxide has partial pressures of 40 mmHg in arterial blood and 45 mmHg in venous blood, fluorocarbons have a carbon dioxide partial pressure of less than 1 mmHg in room air.

An increased carbon dioxide content is always coupled with a low oxygen content in blood. This fixed ratio can be easily offset in an agent by setting increased carbon dioxide contents that result in a vessel dilatation. At the same time, otherwise physiologically optimal oxygen values can be set. An agent containing a nitric oxide can only unfold its action when the partial pressure of oxygen is set such that the competitive reaction of the free radical NO can be sufficiently suppressed with oxygen.

The oxygen-lacking fluorocarbon of the invention can then be used in a known manner in ophthalmology and as described in the aforementioned publications, e.g. as a vitreous body replacement or retina tampon.

In one embodiment, the entire physically dissolved oxygen was first desorped from highly purified perfluorodecalin by rinsing with nitrogen. This process was monitored by oxygen measurements. Based on an oxygen concentration of 8% by volume, a value of 1% by volume was obtained after 30 minutes.

This oxygen-lacking perfluorodecalin was then sterile filtered and injected into one eye each of two rabbits, whereby, prior to the injection, the vitreous body was gas compressed in a known manner. After the gas compression, the gas was intravenously exchanged for 1.2 ml of the deoxygenated perfluorodecalin, so that about two thirds of the vitreous body area, including the area of the retinal blood vessels, was filled with perfluorodecalin.

After durations of between two days and six weeks, the eyes were examined for vessel damage. It was shown that, in comparison to each of the untreated eyes, there was a completely normal condition.

Studies have shown that the substances of the invention are also suitable as an agent in ophthalmology-related fields, in particular as an agent in brain surgery in ischemic-related disorders.

We claim:

1. An oxygen-physiologically acceptable fluorocarbon mixture having a dissolved oxygen content of less than 6-% by volume, wherein the fluorocarbon is selected from the class of saturated, perfluorinated hydrocarbons in which all of the hydrogen atoms are replaced by fluorinated atoms, or partially fluorinated alkanes having the general formula $R_F R_H$ or $R_F R_H R_F$ that can be present in a liquid or gel-like state, and wherein $R_F$ is a perfluorinated alkyl group and $R_H$ is an alkyl group.

2. An oxygen-fluorocarbon mixture according to claim 1, having a dissolved oxygen content of less than 4% by volume.

3. An oxygen-fluorocarbon mixture according to claim 1, having a dissolved oxygen content of less than 1% by volume.

4. An oxygen-fluorocarbon mixture according to claim 1, combined with a second gas, wherein said second gas constitutes between 0 and 20% by volume of the mixture.

5. An oxygen-fluorocarbon mixture according to claim 4 wherein said second gas is selected from the group consisting of carbon dioxide and nitric oxide.

6. A process for preparing an oxygen-physiologically acceptable fluorocarbon mixture having a dissolved oxygen content of less than 6% by volume, wherein the fluorocarbon is selected from the class of saturated, perfluorinated hydrocarbons in which all of the hydrogen atoms are replaced by fluorinated atoms, or partially fluorinated alkanes having the general formula $R_F R_H$ or $R_F R_H R_F$ that can be present in a liquid or gel-like state, wherein $R_F$ is a perfluorinated alkyl group and $R_H$ is an alkyl group; and wherein the fluorocarbon is deoxygenated using a heterogeneous oxygen getter, and stored in an oxygen-lacking state until use.

7. A process according to claim 6 wherein said heterogeneous oxygen getter comprises a low-valence metal oxide.

8. A process according to claim 7, wherein said low-valence metal oxide is reduced $Cu_2O$.

9. A process according to claim 6, wherein said oxygen-lacking state is achieved by hermetic sealing.

10. A process according to claim 6, wherein said oxygen-fluorocarbon mixture is stored in a sealed container with said heterogeneous oxygen getter; and filtered through a sterile filter prior to use.

11. A process according to claim 6, wherein said fluorocarbon is stored in a projecting gas chamber with said heterogeneous oxygen getter, until use.

12. A process according to claim 6, wherein said fluorocarbon is filtered through an absorber cartridge containing said heterogeneous oxygen getter and then filtered through a sterile filter.

13. A process for making an oxygen-physiologically acceptable fluorocarbon mixture having a dissolved oxygen content of less than 6% by volume, wherein the fluorocarbon is selected from the class of saturated, perfluorinated hydrocarbons in which all of the hydrogen atoms are replaced by fluorinated atoms, or partially fluorinated alkanes having the general formula $R_F R_H$ or $R_F R_H R_F$ that can be present in a liquid or gel-like state, and wherein $R_F$ is a perfluorinated alkyl group and $R_H$ is an alkyl group; wherein said fluorocarbon is deoxygenated using a heterogeneous oxygen getter; and proportionately mixed with an oxygen-containing fluorocarbon to obtain a desired oxygen concentration within a range of 0% to 6% by volume; and stored in an oxygen-lacking state until use.

14. A method of using a physiologically acceptable fluorocarbon having a dissolved oxygen content of less than 6% by volume as an agent for ophthalmology, wherein the fluorocarbon is selected from the class of saturated, perfluorinated hydrocarbons in which all of the hydrogen atoms are replaced by fluorinated atoms, or partially fluorinated alkanes having the general formula $R_F R_H$ or $R_F R_H R_F$ that can be present in a liquid or gel-like state, and wherein $R_F$ is a perfluorinated alkyl group and $R_H$ is an alkyl group.

15. A method of use according to claim 14, wherein the dissolved oxygen content is less than 4% by volume.

16. A method of use according to claim 14, wherein the dissolved oxygen content is less than 1% by volume.

17. A method of use according claim 14, wherein the dissolved oxygen content is greater than 0% by volume.

18. A method of use according to claim 14, wherein said fluorocarbon is combined with a second gas to create a mixture, and wherein said second gas constitutes between 1 and 20% by volume of the mixture.

19. A method of using a fluorocarbon according to claim 14, as an intraocular agent.

20. A method of using a fluorocarbon according to claim 17, as an intraocular agent.

21. A method of using a fluorocarbon according to claim 14, as a retina tampon.

22. A method of using a fluorocarbon according to claim 17, as a retina tampon.

23. A method of using a fluorocarbon according to claim 14, as an agent for treating ischemic retinal disorders.

24. A method of using a fluorocarbon according to claim 17, as an agent for treating ischemic retinal disorders.

25. A method of using a fluorocarbon according to claim 14, as a vitreous body replacement.

26. A method of using a fluorocarbon according to claim 17, as a vitreous body replacement.

* * * * *